(12) United States Patent
Yamamoto et al.

(10) Patent No.: US 6,514,529 B2
(45) Date of Patent: Feb. 4, 2003

(54) OXAZOLIDINONE TABLET FORMULATION

(75) Inventors: Ken Yamamoto, Portage, MI (US); Homer Lin, Oak Park, CA (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/809,696

(22) Filed: Mar. 15, 2001

(65) Prior Publication Data

US 2001/0051647 A1 Dec. 13, 2001

Related U.S. Application Data

(60) Provisional application No. 60/190,969, filed on Mar. 22, 2000.

(51) Int. Cl.[7] .......................... A61K 9/20; A61K 9/42; A61K 9/14; A61K 9/16; A61K 9/50
(52) U.S. Cl. .................. 424/465; 424/464; 424/476; 424/489; 424/490; 424/497; 424/499; 424/502
(58) Field of Search ......................... 424/489, 490, 424/497, 499, 502, 464, 465, 476

(56) References Cited

U.S. PATENT DOCUMENTS

| | | | | |
|---|---|---|---|---|
| 3,993,767 A | | 11/1976 | Alphin et al. | 424/272 |
| 5,529,998 A | | 6/1996 | Habich et al. | 514/233.8 |
| 5,547,950 A | * | 8/1996 | Hutchinson et al. | 514/252 |
| 5,627,181 A | | 5/1997 | Riedl et al. | 514/236.8 |
| 5,684,023 A | | 11/1997 | Riedl et al. | 514/337 |
| 5,688,791 A | | 11/1997 | Kimura | 514/224.5 |
| 5,688,792 A | | 11/1997 | Barbachyn et al. | 514/235.5 |
| 5,698,574 A | | 12/1997 | Riedl et al. | 514/376 |
| 5,700,799 A | | 12/1997 | Hutchinson et al. | 514/235.8 |
| 5,792,765 A | | 8/1998 | Riedl et al. | 514/236.8 |
| 5,827,857 A | | 10/1998 | Riedl et al. | 514/301 |
| 5,837,870 A | | 11/1998 | Pearlman et al. | 544/137 |
| 5,843,967 A | | 12/1998 | Riedl et al. | 514/340 |
| 5,861,413 A | | 1/1999 | Habich et al. | 514/312 |
| 5,869,659 A | | 2/1999 | Stolle et al. | 544/114 |
| 5,968,962 A | | 10/1999 | Thomas et al. | 514/376 |
| 5,981,528 A | | 11/1999 | Gravestock et al. | 514/252 |

FOREIGN PATENT DOCUMENTS

| | | | | |
|---|---|---|---|---|
| WO | WO 99/24393 | 5/1999 | ......... | C07C/233/16 |
| WO | WO/00/01378 | 1/2000 | ......... | A61K/31/015 |
| WO | WO/00/73301 A1 | 12/2000 | ......... | C07D/413/04 |

* cited by examiner

Primary Examiner—Thurman K. Page
Assistant Examiner—Humera N. Sheikh
(74) Attorney, Agent, or Firm—John H. Engelmann; Bruce Stein

(57) ABSTRACT

The present invention provides a compressed tablet of an antibacterial oxazolidinone agent which provides high drug load and excellent bioavailability.

19 Claims, No Drawings

OXAZOLIDINONE TABLET FORMULATION

CROSS-REFERENCE TO RELATED APPLICATIONS

This application claims the benefit of the following provisional application: U.S. Ser. No: 60/190,969, filed Mar. 22, 2000, under 35 USC 119(e)(i).

BACKGROUND OF THE INVENTION

1. Field of the Invention

The present invention is a novel tablet formulation which permits high drug load and does not use lactose.

2. Description of the Related Art

Oxazolidinones are well known to those skilled in the art as gram positive anti-bacterial agents, see, for example, U.S. Pat. Nos. 5,688,792, 5,529,998, 5,547,950, 5,627,181, 5,700,799, 5,843,967, 5,792,765, 5,684,023, 5,861,413, 5,827,857, 5,869,659, 5,698,574, 5,968,962 and 5,981,528.

Various tablet formulations are very well known to those skilled in the art which contain starch, microcrystalline cellulose, hydroxypropylcellulose and other ingredients. However, it is very difficult to get high drug load and blood levels similar to IV administration.

SUMMARY OF INVENTION

Disclosed is a compressed tablet containing the following ingredients:
- antibacterial oxazolidinone,
- starch,
- microcrystalline cellulose,
- binder selected from the group consisting of hydroxypropylcellulose, hydroxypropylmethylcellulose, povidone and corn starch paste,
- disintegrants selected from the group consisting of sodium starch glycolate, crosscarmellose sodium, crospovidone and low substituted hydroxypropylcellulose and
- lubricant selected from the group consisting of stearic acid, metalic salts of stearic acid, hydrogenated vegetable oil and talc.

Also disclosed is a method for providing blood levels of an antibacterial oxazolidinone by oral administration medically equivalent to the blood levels produced by IV administration of the same antibacterial oxazolidinone which comprises administration of a compressed tablet of the formulation:
- antibacterial oxazolidinone,
- starch,
- microcrystalline cellulose,
- binder selected from the group consisting of hydroxypropylcellulose, hydroxypropylmethylcellulose, povidone and corn starch paste,
- hydroxypropylcellulose,
- disintegrants selected from the group consisting of sodium starch glycolate, crosscarmellose sodium, crospovidone and low substituted hydroxypropylcellulose and
- lubricant selected from the group consisting of stearic acid, metalic salts of stearic acid, hydrogenated vegetable oil and talc.

DETAILED DESCRIPTION OF THE INVENTION

Oxazolidinones are a new class of gram positive antibacterial agents which are known to those skilled in the art, see for example U.S. Pat. No. 5,688,792. (S)-N-[[3-[3-fluoro-4-(4-morpholinyl)phenyl]-2-oxo-5-oxazolidinyl]methyl]acetamide, known as linezolid, the compound of Example 5 of U.S. Pat. No. 5,688,792 is known and has the following chemical structural formula:

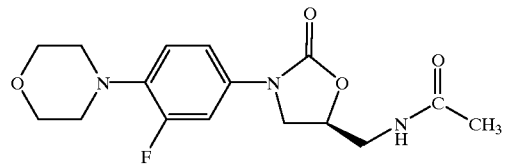

(S)-N-[[3-[3-fluoro-4-[4-(hydroxyacetyl)-1-piperazinyl]-phenyl]-2-oxo-5-oxazolidinyl]methyl]acetamide, known as eperezolid, the compound of Example 8 of U.S. Pat. No. 5,837,870 is known and has the following chemical structural formula:

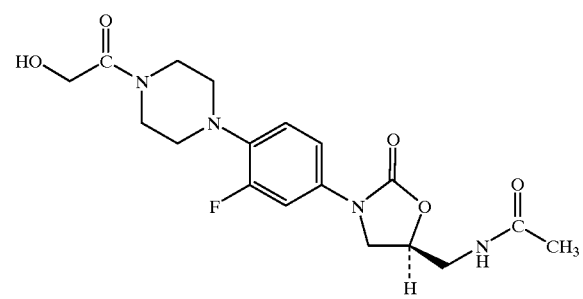

(S)-N-[[3-[3-fluoro-4-(tetrahydro-2H-thiopyran-4-yl)phenyl]-2-oxo-5-oxazolidinyl]methyl]acetamide S,S-dioxide the compound of Example 51 of U.S. Pat. No. 5,968,962 has the following chemical structural formula:

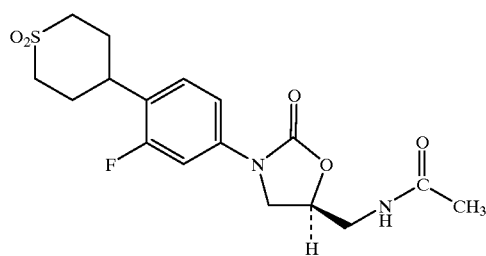

Linezolid and eperezolid can be produced by the processes set forth in U.S. Pat. Nos. 5,688,791 and 5,837,870 as well as that of International Publication W099/24393. They are preferably produced by the process of U.S. Pat. No. 5,837,870. (S)-N-[[3-[3-fluoro-4-(tetrahydro-2H-thiopyran-4-yl)phenyl]-2-oxo-5-oxazolidinyl]methyl]acetamide S,S-dioxide can be produced by the process of U.S. Pat. No. 5,968,962 or the process of U.S. patent application Ser. No. 60/118,150; it is preferred that it be produced by the process of U.S. patent application Ser. No. 60/118,150.

When the antibacterial oxazolidinone is linezolid, it is preferred that linezolid produced be used in crystal form II, which has the characteristics set forth in CHART A. Once linezolid is synthesized, crystal Form II is prepared by starting with linezolid of high enantiomeric purity. It is preferred that the linezolid be more than 98% enantiomerically pure, it is more preferred that the linezolid be more than 99% pure and it is even more preferred that the linezolid be 99.5% pure. The linezolid of greater than 98% enantiomeric purity to be used to form crystal form II can either be in solution or be a solid. The linezolid starting material, solid or solution, is mixed with a solvent selected from the group consisting of compounds of the formula: water, acetonitrile, chloroform, methylene chloride, $R_1$—OH where $R_1$ is $C_1$–$C_6$ alkyl; $R_1$—CO—$R_2$ where $R_2$ is $C_1$–$C_6$ alkyl and $R_1$ is as defined above; phenyl substituted with 1 thru 3 $R_1$ where $R_1$ is as defined above; $R_1$—CO—O—$R_2$ where $R_1$ is $C_1$–$C_6$ alkyl and $R_1$ is as defined above; $R_1$—O—$R_2$ where $R_1$ is $C_1$–$C_6$ alkyl and $R_1$ is as defined above. It is preferred that the solvent be selected from the group consisting of water, ethyl acetate, methanol, ethanol, propanol, isopropanol, butanol, acetonitrile, acetone, methyl ethyl ketone, chloroform, methylene chloride, toluene, xylene, diethyl ether, or methyl-t-butyl ether. It is more preferred that the solvent be ethyl acetate, acetone, acetonitrile, propanol, or isopropanol. It is most preferred that the solvent be ethyl acetate. The mixture of linezolid in the solvent is agitated at a temperature below 80° until crystals of Form II are formed and crystals of other solid forms, such as Form I, disappear. It is preferred to dissolve the linezolid in ethyl acetate at a temperature near the boiling point of the solvent. This mixture is cooled to a temperature of about 70°. The mixture may be seeded with crystals of Form II to facilitate crystallization. It is preferred that the solid product is cooled and agitated at a temperature between about 45° and about 60° until the solids consist only of Form II crystals. It is most preferred to maintain the slurry at a temperature of about 55°. It is preferred to mix the linezolid and solvent for at least 10 min, it is even more preferred to mix the linezolid and solvent for at least 20 min and it is most preferred to mix the linezolid and solvent for at least 30 min. The time and temperature will vary depending on the solvent selected. With ethyl acetate it is preferred to mix for not less that 60 minutes. The crystalline slurry may be further cooled to improve yield, and the solid Form II product may be isolated. The mixture may be further cooled and agitated. Other measures which can be used to facilitate crystallization include, but are not limited to, cooling, concentration of the solution by evaporation or distillation, or through addition of other solvents. The crystals are isolated by procedures known to those skilled in the art.

The preferred solid oral dosage form is a tablet. The composition of the tablets of the present invention can vary but includes the following essential features:

antibacterial oxazolidinone, starch,
microcrystalline cellulose,
binder selected from the group consisting of hydroxypropylcellulose, hydroxypropylmethylcellulose, povidone and corn starch paste,
disintegrants selected from the group consisting of sodium starch glycolate, crosscarmellose sodium, crospovidone and low substituted hydroxypropylcellulose and
lubricant selected from the group consisting of stearic acid, metalic salts of stearic acid, hydrogenated vegetable oil and talc.

It is preferred that the antibacterial oxazolidinone is selected from the group consisting of linezolid, eperezolid and (S)-N-[[3-[3-fluoro-4-(tetrahydro-2H-thiopyran-4-yl) phenyl]-2-oxo-5-oxazolidinyl]methyl]acetamide S,S-dioxide. It is more preferred that the antibacterial oxazolidinone is linezolid. It is preferred that the linezolid is in crystal form II. It is preferred that the starch is corn starch. It is preferred that the binder is hydroxypropylcellulose and that the disintegrant is sodium starch glycolate. It is preferred that the lubricant is magnesium sterarte. It is preferred that the tablet is film coated. It is also preferred that the tablet has a hardness range is from about 18 to about 30 Strong Cobb units; it is more preferred that the tablet has a hardness range is from about 20 to about 25 Strong Cobb units.

When the antibacterial agent is linezolid it is preferred that the linezolid be present in 400 mg or 600 mg amounts; more preferably 600 mg. When linezolid is present in 400 mg, a preferred formulation is:

| | |
|---|---|
| Linezolid | 400.0 mg |
| Corn starch | 36.0–44.0 mg |
| Microcrystalline cellulose (intragranular) | 14.4–17.6 mg |
| Hydroxypropylcellulose (intragranular) | 5.32–6.52 mg |
| Hydroxypropylcellulose (binder solution) | 1.9–2.3 mg |
| Microcrystalline cellulose (extragranular) | 56.1–68.6 mg |
| Sodium starch glycolate | 25.2–30.8 mg |
| Magnesium stearate | 5.04–6.16 mg |

It is more preferred that the 400 mg tablet be coated and have the following formulation:

| | |
|---|---|
| Linezolid | 400.0 mg |
| Corn starch | 36.0–44.0 mg |
| Microcrystalline cellulose (intragranular) | 14.4–17.6 mg |
| Hydroxypropylcellulose (intragranular) | 5.32–6.52 mg |
| Hydroxypropylcellulose (binder solution) | 1.9–2.3 mg |
| Microcrystalline cellulose (extragranular) | 56.1–68.6 mg |
| Sodium starch glycolate | 25.2–30.8 mg |
| Magnesium stearate | 5.04–6.16 mg |
| Opadry White YS-1-18202-A | 11.2–22.4 mg |
| Carnaba Wax | 0–0.224 mg |

It is even more preferred that the 400 mg tablet formulation be:

| | |
|---|---|
| Linezolid | 400.0 mg |
| Corn starch | 40.0 mg |
| Microcrystalline cellulose (intragranular) | 16.0 mg |
| Hydroxypropylcellulose (intragranular) | 5.92 mg |
| Hydroxypropylcellulose (binder solution) | 2.08 mg |
| Microcrystalline cellulose (extragranular) | 62.4 mg |
| Sodium starch glycolate | 28.0 mg |
| Magnesium stearate | 5.6 mg |

It is most preferred that the 400 mg linezolid tablet formulation above be coated:

| | |
|---|---|
| Linezolid | 400.0 mg |
| Corn starch | 40.0 mg |
| Microcrystalline cellulose (intragranular) | 16.0 mg |
| Hydroxypropylcellulose (intragranular) | 5.92 mg |
| Hydroxypropylcellulose (binder solution) | 2.08 mg |
| Microcrystalline cellulose (extragranular) | 62.4 mg |
| Sodium starch glycolate | 28.0 mg |
| Magnesium stearate | 5.6 mg |
| Opadry White YS-1-18202-A | 16.8 mg |
| Carnaba Wax | 0.224 mg |

When linezolid it present in 600 mg, a preferred tablet formulation is:

| Linezolid | 600.0 mg |
| Corn starch | 54–66 mg |
| Microcrystalline cellulose (intragranular) | 21.6–26.4 mg |
| Hydroxypropylcellulose (intragranular) | 7.98–9.78 mg |
| Hydroxypropylcellulose (binder solution) | 2.82–3.42 mg |
| Microcrystalline cellulose (extragranular) | 84.24–102.96 mg |
| Sodium starch glycolate | 37.8–46.2 mg |
| Magnesium stearate | 7.56–9.24 mg |

It is more preferred that the 600 mg linezolid tablet formulation be coated:

| Linezolid | 600.0 mg |
| Corn starch | 54–66 mg |
| Microcrystalline cellulose (intragranular) | 21.6–26.4 mg |
| Hydroxypropylcellulose (intragranular) | 7.98–9.78 mg |
| Hydroxypropylcellulose (binder solution) | 2.82–3.42 mg |
| Microcrystalline cellulose (extragranular) | 84.24–102.96 mg |
| Sodium starch glycolate | 37.8–46.2 mg |
| Magnesium stearate | 7.56–9.24 mg |
| Opadry White YS-1-18202-A | 16.8–33.6 mg |
| Carnaba Wax | 0–0.336 mg |

It is also preferred that the 600 mg linezolid tablet formulation be:

| Linezolid | 600.0 mg |
| Corn starch | 60.0 mg |
| Microcrystalline cellulose (intragranular) | 24.0 mg |
| Hydroxypropylcellulose (intragranular) | 8.88 mg |
| Hydroxypropylcellulose (binder solution) | 3.12 mg |
| Microcrystalline cellulose (extragranular) | 93.6 mg |
| Sodium starch glycolate | 42.0 mg |
| Magnesium stearate | 8.4 mg |

It is most preferred that the 600 mg linezolid tablet be coated:

| Linezolid | 600.0 mg |
| Corn starch | 60.0 mg |
| Microcrystalline cellulose (intragranular) | 24.0 mg |
| Hydroxypropylcellulose (intragranular) | 8.88 mg |
| Hydroxypropylcellulose (binder solution) | 3.12 mg |
| Microcrystalline cellulose (extragranular) | 93.6 mg |
| Sodium starch glycolate | 42.0 mg |
| Magnesium stearate | 8.4 mg |
| Opadry White YS-1-18202-A | 25.2 mg |
| Carnaba Wax | 0.0336 mg |

The above tablet formulations are prepared by methods well known to those skilled in the art. It is preferred that the tablet formulations of the present invention be prepared as follows. The binder solution is prepared by adding part of the hydroxypropylcellulose to the purified water and mixing in an appropriate container until dissolved. The granulation is performed by adding the antibacterial oxazolidinone, corn starch, microcrystalline cellulose (intragranular, 24.0 mg), and the remaining hydroxypropylcellulose into a high shear mixer and mixing until adequately mixed. Then add the binder solution while mixing, and if needed, add an additional sufficient quantity of water while mixing, to form the granulation. Wet screen the granulation using appropriate equipment as is well known to those skilled in the art, for example, a Comil. Following granulation the granulation is dried using suitable equipment, such as a fluid bed dryer. After the granulation is dried, dry screen the granulation using appropriate equipment, such as a Comil. The lubrication portion is formed by mixing microcrystalline cellulose (extragranular, 93.6 mg) and sodium starch glycolate with the dry screened granulation in a suitable blender, such as a diffusion (tumble) type V-blender, until adequately blended. Next remove a portion of the blended material and combine with the magnesium stearate. Add the magnesium stearate mixture back into the blender, such as a diffusion (tumble) type V-blender, and mix until adequately blended. Finally, collect the lubricated powder mixture in appropriate containers.

Alternatively, no binder solution need be used. All the hydroxypropylcellulose can be added as powder. In that situation, the antibacterial oxazolidinone, starch and microcrystalline cellulose and hydroxypropylcellulose are combined, mixed and then the water is added. It is preferred that a binder solution be used.

The compressed tablets are formed using a suitable rotary compression machine and compression tooling. The lubricated powder mixture is compressed into tablets of proper weight, hardness, size and shape.

It is preferred to coat and wax the tablets. The Opadry White YS-1-18202-A and purified water are mixed to prepare the coating suspension. The coating mixture should be continuously stirred until the mixture is free of lumps and the Opadry is in suspension. Prior to using, the film coating suspension should be screened through an appropriate screen. The desired quantity of tablets is loaded into the appropriately sized perforated coating pans (such as an Accela-Cota or Glatt coating pan) equipped with baffles, spray guns and pumping system. The appropriate amount of aqueous film coating is sprayed on the moving tablets until tablets are evenly coated. After the coating is complete, the appropriate amount of carnauba wax is weighed and added to the bed of tablets to polish the film coated tablets.

It is preferred to print the tablets with identifying information as is known to those skilled in the art.

A flow chart of the manufacturing process is provided in CHART B.

The present invention also includes a method for providing blood levels of an antibacterial oxazolidinone by oral administration medically equivalent to the blood levels produced by IV administration of the same antibacterial oxazolidinone which comprises administration of a compressed tablet of the formulation:

antibacterial oxazolidinone, starch, microcrystalline cellulose, binder selected from the group consisting of hydroxypropylcellulose, hydroxypropylmethylcellulose, povidone and corn starch paste, disintegrants selected from the group consisting of sodium starch glycolate, crosscarmellose sodium, crospovidone and low substituted hydroxypropylcellulose and lubricant selected from the group consisting of stearic acid, metalic salts of stearic acid, hydrogenated vegetable oil and talc. All the preferences above with regard to the tablet formulation/composition are preferences for the method of providing blood levels of an antibacterial oxazolidinone by oral administration medically equivalent to the blood levels produced by IV administration of the same antibacterial oxazolidinone.

It is well known to those skilled in the art how to use the oxazolidinone tablets of the present invention. See for example, U.S. Pat. Nos. 5,688,792, 5,547,950 and 5,968,962.

DEFINITIONS AND CONVENTIONS

The definitions and explanations below are for the terms as used throughout this entire document including both the specification and the claims.

DEFINITIONS

Linezolid refers to (S)-N-[[3-[3-fluoro-4-(4-morpholinyl)phenyl]-2-oxo-5-oxazolidinyl]methyl]acetamide is the compound of formula:

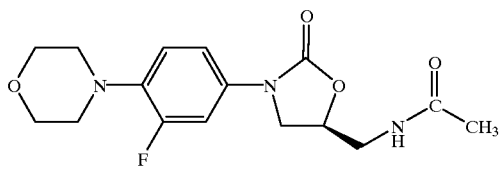

Eperezolid refers to (S)-N-[[3-[3-fluoro-4-[4-(hydroxyacetyl)-1-piperazinyl]-phenyl]-2-oxo-5-oxazolidinyl]methyl]acetamide is the compound of formula:

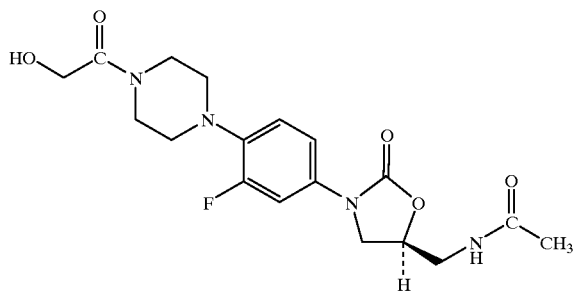

All temperatures are in degrees Celsius.

USP refers to the United States Pharmacopiea.

NF refers to the National Formulary.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

Opadry White refers to Colorcon's tablet coating product. The product code YS-1-18202-A refers to a specific tablet coating formula.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Linezolid (400 mg) Tablet Formulation

| Ingredients | Amount |
| --- | --- |
| Linezolid | 400.0 mg |
| Corn starch NF | 40.0 mg |
| Microcrystalline cellulose NF | 16.0 mg |
| Hydroxypropylcellulose (intragranular) NF | 5.92 mg |
| Hydroxypropylcellulose (binder solution) NF | 2.08 mg |
| Microcrystalline cellulose NF | 62.4 mg |
| Sodium starch glycolate NF | 28.0 mg |
| Magnesium stearate NF | 5.6 mg |
| Purified water USP 22.0% uncoated tablet wt | |
| Film Coating Phase | |
| Opadry White YS-1-18202-A | 16.8 mg |
| Purified Water USP | 129.2 mg |
| Polishing Phase | |
| Carnauba Wax NF | 0.0224 mg |

The binder solution is prepared by adding part of the hydroxypropylcellulose to the purified water and mixing in an appropriate container until dissolved. The granulation is performed by adding the antibacterial oxazolidinone, corn starch, microcrystalline cellulose (intragranular, 24.0 mg), and the remaining hydroxypropylcellulose into a high shear mixer and mixing until adequately mixed. Then add the binder solution while mixing, and if needed, add an additional sufficient quantity of water while mixing, to form the granulation. Wet screen the granulation using appropriate equipment as is well known to those skilled in the art, for example, a Comil. Following granulation the granulation is dried using suitable equipment, such as a fluid bed dryer. After the granulation is dried, dry screen the granulation using appropriate equipment, such as a Comil. The lubrication portion is formed by mixing microcrystalline cellulose (extragranular, 93.6 mg) and sodium starch glycolate with the dry screened granulation in a suitable blender, such as a diffusion (tumble) type V-blender, until adequately blended. Next remove a portion of the blended material and combine with the magnesium stearate. Add the magnesium stearate mixture back into the blender, such as a diffusion (tumble) type V-blender, and mix until adequately blended. Finally, collect the lubricated powder mixture in appropriate containers.

The compressed tablets are formed using a suitable rotary compression machine and compression tooling. The lubricated powder mixture is compressed into tablets of proper weight, hardness, size and shape.

It is preferred to coat and wax the tablets. The Opadry White YS-1-18202-A and purified water are mixed to prepare the coating suspension. The coating mixture should be continuously stirred until the mixture is free of lumps and the Opadry is in suspension. Prior to using, the film coating suspension should be screened through an appropriate screen. The desired quantity of tablets is loaded into the appropriately sized perforated coating pans (such as an Accela-Cota or Glatt coating pan) equipped with baffles, spray guns and pumping system. The appropriate amount of aqueous film coating is sprayed on the moving tablets until tablets are evenly coated. After the coating is complete, the appropriate amount of carnauba wax is weighed and added to the bed of tablets to polish the film coated tablets.

It is preferred to print the tablets with identifying information as is known to those skilled in the art.

A flow chart of the manufacturing process is provided in CHART B.

Example 2

Linezolid (600 mg) Tablet Formulation

| Ingredients | Amount |
|---|---|
| Linezolid | 600.0 mg |
| Corn starch NF | 60.0 mg |
| Microcrystalline cellulose NF | 24.0 mg |
| Hydroxypropylcellulose (intragranular) NF | 8.88 mg |
| Hydroxypropylcellulose (binder solution) NF | 3.12 mg |
| Microcrystalline cellulose NF | 93.6 mg |
| Sodium starch glycolate NF | 42.0 mg |
| Magnesium stearate NF | 8.4 mg |
| Purified water USP 22.0% uncoated tablet wt | |
| Film Coating Phase | |
| Opadry White YS-1-18202-A | 25.2 mg |
| Purified Water USP | 193.9 mg |
| Polishing Phase | |
| Carnauba Wax NF | 0.0336 mg |

Following the general procedure of EXAMPLE 1 and making non-critical variations but using the amounts of ingredients above Linezolid 600 mg tablets are produced.

Chart A

Linezolid, (S)-N-[[3-[3-fluoro-4-(4-morpholinyl)phenyl]-2-oxo-5-oxazolidinyl]methyl]acetamide, crystal "Form II" has the powder X-ray diffraction spectrum of:

| d-Spacing (Å) | Two-Theta Angle (°) | Relative Intensity (%) |
|---|---|---|
| 12.44 | 7.10 | 2 |
| 9.26 | 9.54 | 9 |
| 6.37 | 13.88 | 6 |
| 6.22 | 14.23 | 24 |
| 5.48 | 16.18 | 3 |
| 5.28 | 16.79 | 100 |
| 5.01 | 17.69 | 2 |
| 4.57 | 19.41 | 4 |
| 4.50 | 19.69 | 2 |
| 4.45 | 19.93 | 6 |
| 4.11 | 21.61 | 15 |
| 3.97 | 22.39 | 23 |
| 3.89 | 22.84 | 4 |
| 3.78 | 23.52 | 7 |
| 3.68 | 24.16 | 1 |
| 3.52 | 25.28 | 13 |
| 3.34 | 26.66 | 1 |
| 3.30 | 27.01 | 3 |
| 3.21 | 27.77 | 1 | and an infrared (IR) spectrum (mineral oil mull) of 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852 and 758 cm$^{-1}$.

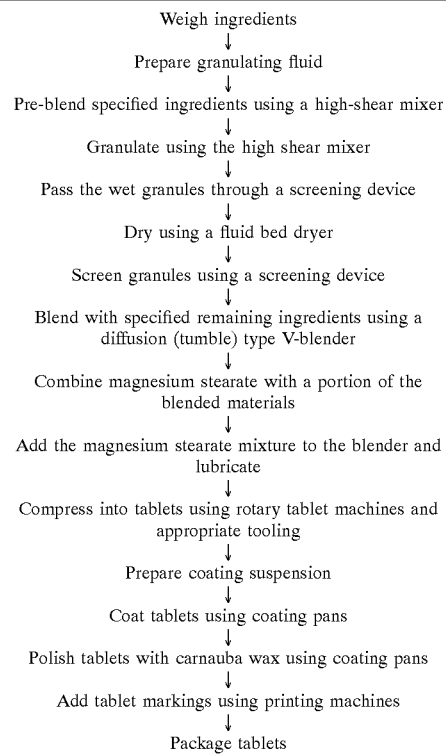

Linezolid Tablet Manufacturing Flowchart

Weigh ingredients ↓
Prepare granulating fluid ↓
Pre-blend specified ingredients using a high-shear mixer ↓
Granulate using the high shear mixer ↓
Pass the wet granules through a screening device ↓
Dry using a fluid bed dryer ↓
Screen granules using a screening device ↓
Blend with specified remaining ingredients using a diffusion (tumble) type V-blender ↓
Combine magnesium stearate with a portion of the blended materials ↓
Add the magnesium stearate mixture to the blender and lubricate ↓
Compress into tablets using rotary tablet machines and appropriate tooling ↓
Prepare coating suspension ↓
Coat tablets using coating pans ↓
Polish tablets with carnauba wax using coating pans ↓
Add tablet markings using printing machines ↓
Package tablets

What is claimed is:

1. A compressed tablet which contains:

| | |
|---|---|
| Linezolid | 400.0 mg |
| Corn starch | 36.0–44.0 mg |
| Microcrystalline cellulose | 70.5–86.2 mg |
| Hydroxypropylcellulose | 7.2–8.8 mg |
| Sodium starch glycolate | 25.2–30.8 mg |
| Magnesium stearate | 5.04–6.16 mg. |

2. A compressed tablet according to claim 1 which contains:

| | |
|---|---|
| Linezolid | 400.0 mg |
| Corn starch | 36.0–44.0 mg |
| Microcrystalline cellulose | 70.5–86.2 mg |
| Hydroxypropylcellulose | 7.2–8.8 mg |
| Sodium starch glycolate | 25.2–30.8 mg |
| Magnesium stearate | 5.04–6.16 mg |
| Opadry White YS-1-18202-A | 11.2–22.4 mg |
| Carnaba Wax | 0–0.0224 mg |

3. A compressed tablet according to claim 1 which contains:

| | |
|---|---|
| Linezolid | 400.0 mg |
| Corn starch | 40.0 mg |
| Microcrystalline cellulose | 78.4 mg |
| Hydroxypropylcellulose | 8.00 mg |

-continued

| | |
|---|---|
| Sodium starch glycolate | 28.0 mg |
| Magnesium stearate | 5.6 mg |

4. A compressed tablet according to claim 3 which contains:

| | |
|---|---|
| Linezolid | 400.0 mg |
| Corn starch | 40.0 mg |
| Microcrystalline cellulose | 78.4 mg |
| Hydroxypropylcellulose | 8.00 mg |
| Sodium starch glycolate | 28.0 mg |
| Magnesium stearate | 5.6 mg |
| Opadry White YS-1-18202-A | 16.8 mg |
| Carnaba Wax | 0.0224 mg |

5. A compressed tablet according to claim 1 which contains:

| | |
|---|---|
| Linezolid | 600.0 mg |
| Corn starch | 54–66 mg |
| Microcrystalline cellulose | 105.84–129.36 mg |
| Hydroxypropylcellulose | 10.8–13.2 mg |
| Sodium starch glycolate | 37.8–46.2 mg |
| Magnesium stearate | 7.56–9.24 mg |

6. A compressed tablet according to claim 5 where:

| | |
|---|---|
| Linezolid | 600.0 mg |
| Corn starch | 54–66 mg |
| Microcrystalline cellulose | 105.84–129.36 mg |
| Hydroxypropylcellulose | 10.8–13.2 mg |
| Sodium starch glycolate | 37.8–46.2 mg |
| Magnesium stearate | 7.56–9.24 mg |
| Opadry White YS-1-18202-A | 16.8–33.6 mg |
| Carnaba Wax | 0–0.0336 mg |

7. A compressed tablet according to claim 5 where:

| | |
|---|---|
| Linezolid | 600.0 mg |
| Corn Starch | 60.0 mg |
| Microcrystalline cellulose | 117.6 mg |
| Hydroxypropylcellulose | 12.00 mg |
| Sodium starch glycolate | 42.0 mg |
| Magnesium stearate | 8.4 mg |

8. A compressed tablet according to claim 7 where:

| | |
|---|---|
| Linezolid | 600.0 mg |
| Corn starch | 60.0 mg |
| Microcrystalline cellulose | 117.6 mg |
| Hydroxypropylcellulose | 12.00 mg |
| Sodium starch glycolate | 42.0 mg |
| Magnesium stearate | 8.4 mg |
| Opadry White YS-1-18202-A | 25.2 mg |
| Carnaba Wax | 0.0336 mg |

9. A method for providing blood levels of an antibacterial oxazolidinone by oral administration medically equivalent to the blood levels produced by IV administration of the same antibacterial oxazolidinone which comprises administration of a compressed tablet of the formulation:

antibacterial oxazolidinone,
starch,
microcrystalline cellulose,
binder selected from the group consisting of hydroxypropylcellulose, hydroxypropylmethylcellulose, povidone and corn starch paste,
hydroxypropylcellulose,
disintegrants selected from the group consisting of sodium starch glycolate, crosscarmellose sodium, crospovidone and low substituted hydroxypropylcellulose and
lubricant selected from the group consisting of stearic acid, metalic salts of stearic acid, hydrogenated vegetable oil and talc.

10. A method according to claim 9 where the antibacterial oxazolidinone is selected from the group consisting of linezolid, eperezolid and (S)-N-[[3-[3-fluoro-4-(tetrahydro-2H-thiopyran-4-yl)phenyl]-2-oxo-5-oxazolidinyl]methyl] acetamide S,S-dioxide.

11. A compressed tablet according to claim 10 where the antibacterial oxazolidinone is selected from the group consisting of linezolid.

12. A method according to claim 11 where the compressed tablet contains:

| | |
|---|---|
| Linezolid | 400.0 mg |
| Corn starch | 36.0–44.0 mg |
| Microcrystalline cellulose | 70.5–86.2 mg |
| Hydroxypropylcellulose | 7.2–8.8 mg |
| Sodium starch glycolate | 25.2–30.8 mg |
| Magnesium stearate | 5.04–6.16 mg |

13. A method according to claim 12 where the compressed tablet contains:

| | |
|---|---|
| Linezolid | 400.0 mg |
| Corn starch | 36.0–44.0 mg |
| Microcrystalline cellulose | 70.5–86.2 mg |
| Hydroxypropylcellulose | 7.2–8.8 mg |
| Sodium starch glycolate | 25.2–30.8 mg |
| Magnesium stearate | 5.04–6.16 mg |
| Opadry White YS-1-18202-A | 11.2–22.4 mg |
| Carnaba Wax | 0–0.0224 mg |

14. A method according to claim 12 where the compressed tablet contains:

| | |
|---|---|
| Linezolid | 400.0 mg |
| Corn starch | 40.0 mg |
| Microcrystalline cellulose | 78.4 mg |
| Hydroxypropylcellulose | 8.00 mg |
| Sodium starch glycolate | 28.0 mg |
| Magnesium stearate | 5.6 mg |

15. A method according to claim 14 where the compressed tablet contains:

| | |
|---|---|
| Linezolid | 400.0 mg |
| Corn starch | 40.0 mg |
| Microcrystalline cellulose | 78.4 mg |

-continued

| | |
|---|---|
| Hydroxypropylcellulose | 8.00 mg |
| Sodium starch glycolate | 28.0 mg |
| Magnesium stearate | 5.6 mg |
| Opadry White YS-1-18202-A | 16.8 mg |
| Carnaba Wax | 0.0224 mg |

16. A method according to claim 11 where the compressed tablet contains:

| | |
|---|---|
| Linezolid | 600.0 mg |
| Corn starch | 54–66 mg |
| Microcrystalline cellulose | 105.84–129.36 mg |
| Hydroxypropylcellulose | 10.8–13.2 mg |
| Sodium starch glycolate | 37.8–46.2 mg |
| Magnesium stearate | 7.56–9.24 mg |

17. A method according to claim 16 where the compressed tablet contains:

| | |
|---|---|
| Linezolid | 600.0 mg |
| Corn starch | 54–66 mg |
| Microcrystalline cellulose | 105.84–129.36 mg |
| Hydroxypropylcellulose | 10.8–13.2 mg |
| Sodium starch glycolate | 37.8–46.2 mg |
| Magnesium stearate | 7.56–9.24 mg |

-continued

| | |
|---|---|
| Opadry White YS-1-18202-A | 16.8–33.6 mg |
| Carnaba Wax | 0–0.0336 mg |

18. A method according to claim 16 where the compressed tablet contains:

| | |
|---|---|
| Linezolid | 600.0 mg |
| Corn starch | 60.0 mg |
| Microcrystalline cellulose | 117.6 mg |
| Hydroxypropylcellulose | 12.00 mg |
| Sodium starch glycolate | 42.0 mg |
| Magnesium stearate | 8.4 mg |

19. A method according to claim 18 where the compressed tablet contains:

| | |
|---|---|
| Linezolid | 600.0 mg |
| Corn starch | 60.0 mg |
| Microcrystalline cellulose | 117.6 mg |
| Hydroxypropylcellulose | 12.00 mg |
| Sodium starch glycolate | 42.0 mg |
| Magnesium stearate | 8.4 mg |
| Opadry White YS-1-18202-A | 25.2 mg |
| Carnaba Wax | 0.0336 mg |

\* \* \* \* \*